United States Patent [19]

Ward et al.

[11] Patent Number: 5,037,992

[45] Date of Patent: Aug. 6, 1991

[54] PROCESS FOR SULFATING UNSATURATED ALCOHOLS

[75] Inventors: James F. Ward, Fairfield; Randall S. Matthews, Cincinnati, both of Ohio

[73] Assignee: The Procter & Gamble Company, Cincinnati, Ohio

[21] Appl. No.: 451,840

[22] Filed: Dec. 18, 1989

[51] Int. Cl.$^5$ ................................. C07C 141/10
[52] U.S. Cl. ..................................... 558/36
[58] Field of Search ........................... 558/36

[56] References Cited

U.S. PATENT DOCUMENTS

| | | |
|---|---|---|
| 1,968,793 | 7/1934 | Bertsch . |
| 2,044,919 | 6/1936 | Schrauth et al. . |
| 2,060,254 | 11/1936 | Siebenburger . |
| 2,075,914 | 4/1937 | Snoddy et al. . |
| 2,079,347 | 5/1937 | Hailwood . . |
| 2,099,214 | 11/1937 | McAllister . |
| 2,199,399 | 5/1940 | Engelmann . |
| 2,235,098 | 3/1941 | Brandt et al. . |
| 2,335,193 | 11/1943 | Nawiasky et al. . |
| 2,640,070 | 5/1953 | Dahmen . |
| 2,957,014 | 10/1960 | Smith et al. . |
| 3,172,901 | 3/1965 | Miyamoto et al. . |
| 3,332,979 | 7/1967 | Redemann . |
| 3,778,479 | 12/1973 | Morrisroe et al. . |
| 4,226,797 | 10/1980 | Bakker et al. . |
| 4,464,292 | 8/1984 | Lengyel . |

FOREIGN PATENT DOCUMENTS

| | | |
|---|---|---|
| 336332 | 5/1972 | U.S.S.R. . |
| 691929 | 5/1953 | United Kingdom . |
| 1283436 | 7/1972 | United Kingdom . |

OTHER PUBLICATIONS

E. E. Gilbert, "Recent Developments in Preparative Sulfonation and Sulfation", Synthesis–Int'l. J. of Methods in Synth. Org. Chem., vol. 1, No. 1, pp. 3–10, 1969.

N. R. Pai, "Sulphated Factory Alcohols", Textile Dyer & Printer, 14(7), pp. 27–33, 1981.

J. K. Weil, A. J. Stirton and E. B. Leardi, "Ether Alcohol Sulfates from Oleyl Alcohol", J. Am. Oil Chem. Soc., vol. 44, pp. 522–524, (1967).

J. K. Weil, A. J. Stirton and R. G. Bistline Jr., "Synthetic Detergents from Animal Fats. The Sulfation of Tallow Alcohols", J. Am. Oil Chem. Soc., vol. 31, pp. 444–447, (1954).

A. J. Stirton, J. K. Weil, A. A. Stawitzke and S. James, "Synthetic Detergents from Animal Fats. Disodium Alpha–Sulfopalmitate and Sodium Oleyl Sulate", J. Am. Oil Chem. Soc., vol. 29, pp. 198–201. (1952).

D. Nowak, K. Linkiewicz, "Sulfating of Unsaturated Aliphatic Alcohols by Gaeous Sulfur Trixode", Przem. Chem. 1971, 50(4), 222–5 (Pol.)–(Abstract Attached).

*Primary Examiner*—Nicky Chan
*Attorney, Agent, or Firm*—R. C. Witte; J. J. Yetter; R. A. Dabek

[57] ABSTRACT

The present invention is directed to a process for sulfating unsaturated alcohols using inexpensive reagents and mild reaction conditions. The process comprises reacting an unsaturated alcohol of the formula R—OH, wherein R is a $C_8$–$C_{22}$ alkenyl group, with an ether sulfate of the formula $R^1(OCH_2CH_2)_nOSO_3M$, wherein $R^1$ is a $C_1$–$C_{18}$ hydrocarbyl group, n is an integer from 1 to 10, and M is an alkali metal, to form an unsaturated sulfate; said reaction being carried out in the presence of a catalytically effective amount of an acid catalyst. The mole ratio of unsaturated alcohol reactant to ether sulfate ranges from about 0.5:1 to about 2:1. In this process the sulfation occurs primarily at the hydroxyl group of the unsaturated alcohol, with minimal sulfation at the olefinic moiety of said alcohol.

18 Claims, No Drawings

5,037,992

PROCESS FOR SULFATING UNSATURATED ALCOHOLS

TECHNICAL FIELD

The present invention relates to a process for sulfating unsaturated fatty alcohols. In particular, it relates to a process in which an ether sulfate is reacted with an unsaturated fatty alcohol in the presence of an acid catalyst to form an unsaturated fatty sulfate.

BACKGROUND OF THE INVENTION

Unsaturated fatty sulfates are excellent surfactants and are widely utilized in heavy duty detergents, light duty liquids, shampoos and other cleaning products. Certain types of unsaturated fatty sulfates, such as sodium oleyl sulfate, are especially preferred surfactants due to their solubility, foaming, detergency and mildness properties. Therefore, it would be desirable to develop a method for preparing such unsaturated fatty sulfates in an inexpensive manner, such as by using inexpensive reagents and reacting the reagents under mild reaction conditions. The sulfation of unsaturated alcohols, however, is complicated by the ease with which common sulfating agents react at the carbon-carbon double bond of the unsaturated alcohol reactant. Sulfation at the carbon-carbon double bond can result in a saturated compound which has reduced effectiveness for cleaning applications.

Processes for sulfating unsaturated fatty alcohols are known in the art. U.S. Pat. No. 2,079,347, issued May 4, 1937, to Hailwood, discloses a process for preparing unsaturated sulfate esters wherein unsaturated long-chain alcohols, or mixtures thereof, are treated with the addition product of sulfur trioxide and an amine. In the disclosed process the unsaturated long-chain alcohols are converted into their sulfuric esters, or salts thereof, without attack on their unsaturated linkages.

U.S. Pat. No. 2,099,214, issued Nov. 16, 1937, to McAllister, discloses a process for sulfating unsaturated alcohols wherein said alcohols are reacted with a reagent consisting of the addition product of sulfur trioxide and dioxane. Chlorosulfonic acid may be substituted for sulfur trioxide in preparing the addition product reactant.

U.S. Pat. No. 2,060,254, issued Nov. 10, 1936, to Siebenburger, discloses a process for reacting unsaturated fatty alcohols with the addition compound of sulfur trioxide and a liquid organic base, in the presence of excess organic base, to form sulfuric acid esters of said alcohols. The sulfuric acid esters are prepared in a condition free from other sulfonation products, such as are formed by replacement of a hydrogen atom by a $SO_3H$ group or by addition of a sulfuric acid residue at an unsaturated linkage.

U.S. Pat. No. 2,075,914, issued Apr. 6, 1937, to Snoddy et al., discloses a process for sulfating unsaturated alcohols with reagents prepared by (a) reacting sulfur trioxide with a metal chloride, or (b) reacting chlorosulfonic acid with a metal chloride or a metal sulfate.

Processes for sulfating unsaturated fatty compounds are also known in the art. U.S. Pat. No. 2,335,193, issued Nov. 23, 1943, to Nawiasky et al., discloses a process for preparing an olefinic sulfonic acid wherein olefins are sulfonated or sulfated with the addition product of 1,4-thioxane and sulfuric acid derivatives, specifically $SO_3$ and $HSO_3Cl$. In the disclosed sulfation (or sulfonation) reaction the double bond of the original olefin reactant remains unreacted.

U.S. Pat. No. 4,226,797, issued Oct. 7, 1980, to Bakker et al., discloses a process for preparing a secondary $C_8-C_{22}$ monoalkyl sulfuric acid, said process comprising sulfating one or more $C_8-C_{22}$ olefins with sulfuric acid in the presence of at least 15% of $C_8-C_{22}$ secondary alcohols.

None of the above referenced reactions, however, facilitate the sulfation of unsaturated alcohols with an ether sulfate under mild reaction conditions while at the same time providing an unsaturated fatty sulfate product which is sulfated primarily at the hydroxyl group of the original alcohol reactant. This is desirable in that a purer product will be obtained without the discoloration experienced when sulfation occurs at other reaction sites of the molecule.

It is therefore an object of the present invention to provide a process for sulfating unsaturated fatty alcohols with an ether sulfate under mild reaction conditions to form an unsaturated sulfate compound which is sulfated primarily at the hydroxyl group of the original alcohol reactant.

This object is realized by the present invention.

SUMMARY OF THE INVENTION

The present invention is directed to a process for sulfating unsaturated alcohols, said process comprising reacting an unsaturated alcohol of the formula R—OH, wherein R is a $C_8-C_{22}$ alkenyl group, with an ether sulfate of the formula $R^1(OCH_2CH_2)_nOSO_3M$, wherein $R^1$ is a $C_1-C_{18}$ hydrocarbyl group, n is an integer from 1 to 10, inclusive, and M is an alkali metal, and wherein the mole ratio of unsaturated alcohol reactant to ether sulfate reactant ranges from about 0.5:1 to about 2:1, to form an unsaturated sulfate compound of the formula R—$OSO_3M$; said reaction being carried out in the presence of a catalytically effective amount of an acid catalyst.

DETAILED DESCRIPTION OF THE INVENTION

In accordance with this invention, a process is described herein for sulfating an unsaturated alcohol using inexpensive sulfating agents, thereby obtaining a higher quality product than obtainable with known sulfation processes for unsaturated alcohols. In the disclosed process, sulfation occurs primarily at the hydroxyl group of the unsaturated alcohol.

In the sulfation process of the present invention, an unsaturated alcohol reactant of the formula R—OH, wherein R is a $C_8-C_{22}$ alkenyl group, preferably a $C_{15}C_{21}$ alkenyl group, most preferably an oleyl group, is sulfated by reacting with an ether sulfate reactant. R may be a branched-chain or straight-chain alkenyl group, with straight-chain being preferred. The mole ratio of unsaturated alcohol reactant to ether sulfate reactant ranges from about 0.5:1 to about 2:1, preferably from about 0.66:1 to about 1.5:1, most preferably at a mole ratio of about 1:1.

The unsaturated alcohol reactant may either be reacted directly with the ether sulfate, or may be dissolved in a solvent to form an initial reaction mixture, which is then reacted with the ether sulfate. When the unsaturated alcohol reactant is dissolved in a solvent prior to reacting with the ether sulfate reactant, the weight ratio of solvent to unsaturated alcohol reactant ranges from about 1:1 to about 10:1, preferably from about 2:1 to about 5:1, most preferably about 3:1. Solvents useful herein include ethers and other organic compounds. Examples of unsaturated alcohols useful as reactants in the present invention include oleyl alcohol, cis-11-hexadecen-1-ol, 3,7,11,15-tetramethyl-2-hexadecen-1-ol, cis-7-tetradecen-1-ol, cis-7-dodecen-1-ol, with oleyl alcohol being most preferred. Examples of ether compounds useful as solvents in the present invention include dioxane, THF, diethyl ether, and other ethers. Examples of other organic compounds useful as solvents in the present invention include methylene chloride and hexane. The most preferred of these solvents is diethyl ether. It is important to note that alcohols cannot be used as solvents in the process of the present invention.

The ether sulfate reactant of the present invention is of the formula $R^1(OCH_2CH_2)_nOSO_3M$, wherein R is a $C_1-C_{18}$ hydrocarbyl group, preferably a $C_1-C_6$ alkyl group, most preferably methyl, n is an integer ranging from 1 to 10, preferably from 1 to 4, most preferably 1, and M is an alkali metal, preferably sodium. This ether sulfate reactant is added directly to the unsaturated alcohol. If a solvent is utilized, the ether sulfate reactant is added to the initial reaction mixture containing the unsaturated alcohol and solvent, thus forming a secondary reaction mixture. Examples of sulfating agents useful in the present invention include sodium methoxyethyl sulfate and sodium methoxyethoxy ethyl sulfate, with sodium methoxyethyl sulfate being most preferred. The ether sulfate reactant may be prepared by sulfating an ether alcohol via methods known in the art.

The sulfation reaction is carried out in the presence of an acid catalyst, preferably a strong acid or an organic acid. The acid is added to the unsaturated alcohol and ether sulfate mixture, or to the secondary reaction mixture if a solvent is being utilized, typically with agitation, to form a final reaction mixture. For the purposes of this application, strong acids are acids which ionize essentially completely in water, producing a hydrogen ion and an anion.

Examples of strong acids suitable for use in the present process include hydrochloric acid, hydrobromic acid, hydroiodic acid, nitric acid, perchloric acid and sulfuric acid, with sulfuric acid being preferred. Examples of organic acids suitable for use in the present invention include Amberlyst ® 15, available from Aldrich Chemical Company, Inc., Milwaukee, Wisconsin, polystyrene sulfonic acid, toluene sulfonic acid, camphorsulfonic acid and methane sulfonic acid, with methane sulfonic acid and toluene sulfonic acid, being preferred. Sulfuric acid is the most preferred acid catalyst. The mole ratio of acid catalyst to unsaturated alcohol reactant typically effective for the process of the present invention ranges from about 1:100 to about 1:5, preferably from about 3:100 to about 1:10, most preferably about 1:20.

The mechanism of sulfation in the process of the present invention is transsulfation. The following is an example of this reaction process:

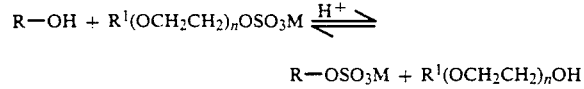

$$R-OSO_3M + R^1(OCH_2CH_2)_nOH$$

wherein R, $R^1$, n and M are as hereinbefore defined. The above reaction is typically driven to completion by removal of the ethoxylated alcohol product, and as such it is preferably that n be a low number so as to facilitate removal of said alcohol.

The sulfation reaction described above is carried out at temperatures ranging from about 0° C. to about 50° C., preferably at temperatures ranging from about 20° C. to about 40° C., most preferably between about 20° C. and about 25° C.

The reaction between the ether sulfate and unsaturated alcohol reactants described above is generally carried out for a period of time ranging from about 4 hours to about 48 hours, with a period of from about 12 hours to about 36 hours being more typical, and a period of about 18 hours being most typical.

In the process of the present invention, the sulfation reaction occurs primarily at the hydroxyl group of the unsaturated alcohol reactant. Typically, about 90%, more typically about 95%, most typically in excess of 99% of the initial unsaturated alcohol reactant is sulfated at its hydroxyl group. While not intending to be bound by theory, it is believed that the ether group in the sulfate reactant exerts a moderating affect on the sulfation reaction, thus preventing sulfonation side reactions and reactions at the double bond of the unsaturated alcohol. An additional benefit associated with the ether sulfate reactant is that substantially no isomerization of the sulfate product to the elaidyl compound occurs. A further benefit is that the ether sulfate reactant is a stable salt and reacts to form a sulfated product which is also a stable salt.

The final reaction mixture typically comprises from about 35% to about 70% by weight, preferably from about 37% to about 60% by weight, most preferably about 59% by weight of unsaturated alcohol; from about 30% to about 70% by weight, preferably from about 35% to about 65% by weight, most preferably about 40% by weight of ether sulfate reactant; and from about 0.5% to about 10% by weight, preferably from about 1% to about 8% by weight, most preferably about 1% by weight of acid catalyst. When the reaction is carried out in the presence of a solvent, the solvent will typically comprise from about 45% to about 75% by weight, preferably from about 50% to about 70% by weight, most preferably about 60% by weight of the final reaction mixture.

The product resulting from the above sulfation reaction will typically comprise from about 6% to about 15% by weight, more typically from about 8% to about 12% by weight, most typically about 10% by weight, of the unsaturated sulfate compound of the formula R—O-SO$_3$M, wherein R and M are as hereinbefore defined; from about 3% to about 25% by weight, more typically from about 5% to about 15% by weight, most typically about 8% by weight of the ethoxylated alcohol compound of the formula $R^1(OCH_2CH_2)_nOH$, wherein $R^1$ and n are as hereinbefore defined; from about 0.1% to about 5% by weight, more typically from about 0.2% to about 2% by weight; most typically about 0.4% by weight of the acid catalyst; and from 0% to about 70% by weight, more typically from about 30% to about 65% by weight, most typically about 60% by weight of solvent; with the balance comprising the initial reactants and reaction by-products.

In the most preferred embodiment of the present invention, equimolar quantities of sodium methoxyethyl sulfate and oleyl alcohol are reacted in the presence of catalytic quantities of sulfuric acid at ambient temperature to form sodium oleyl sulfate and methoxyethanol. This reaction proceeds as follows:

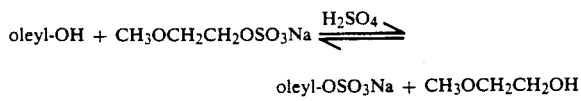

oleyl-OH + CH$_3$OCH$_2$CH$_2$OSO$_3$Na $\xrightleftharpoons{\text{H}_2\text{SO}_4}$ oleyl-OSO$_3$Na + CH$_3$OCH$_2$CH$_2$OH This reaction is driven to completion by removing the methoxyethanol as it is formed. The initial sodium methoxyethyl sulfate reactant may be formed by sulfating methoxyethyl alcohol via methods known in the art.

The reaction product of the process of the present invention may be used in laundry detergent compositions, as described herein.

DETERGENT COMPOSITIONS

Laundry care compositions may be prepared containing the reaction product of the process of the present invention. Such compositions are especially suitable for textile laundering operations. Both solid and liquid detergent compositions can be prepared using the reaction product of this invention. Such composition typically contain from about 1% by weight to about 40% by weight of the reaction product of this invention.

Optional Detergent Components

Laundry care compositions prepared using the product of the process of the present invention can also contain conventional detergent components and adjuvants at their art-established levels.

Detersive Surfactants

The surfactant component can comprise as little as about 1% of the laundry care compositions herein, but preferably the compositions will contain from about 5% to about 40%, more preferably from about 10% to about 30%, of surfactant.

Combinations of anionic (preferably linear alkyl benzene sulfonates) and nonionic (preferably alkyl polyethoxylated alcohols) surfactants are preferred for optimum combined cleaning and textile softening performance, but other classes of surfactants, such as semipolar, ampholytic, zwitterionic, and cationic may be used. Mixtures of these surfactants can also be used.

A. Nonionic Detergent Surfactants

Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Classes of useful nonionic surfactants include:

1. The polyethylene oxide condensates of alkyl phenols. These compounds include the condensation products of alkyl phenols having an alkyl group containing from about 6 to about 12 carbon atoms in either a straight chain or branched chain configuration with ethylene oxide, the ethylene oxide being present in an amount equal to from about 5 to about 25 moles of ethylene oxide per mole of alkyl phenol. Examples of compounds of this type include nonyl phenol condensed with about 9.5 moles of ethylene oxide per mole of phenol; dodecyl phenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal TM CO-630, marketed by the GAF Corporation; and Triton TM X-45, X-114, X-100, and X-102, all marketed by the Rohm & Haas Company.

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 4 to about 10 moles of ethylene oxide per mole of alcohol. Examples of such ethoxylated alcohols include the condensation product of myristyl alcohol with about 10 moles of ethylene oxide per mole of alcohol; and the condensation product of coconut alcohol (a mixture of fatty alcohols with alkyl chains varying in length from 10 to 14 carbon atoms) with about 9 moles of ethylene oxide. Examples of commercially available nonionic surfactants of this type include Tergitol TM 15-S-9 (the condensation product of C$_{11}$–C$_{15}$ linear alcohol with 9 moles ethylene oxide), Tergitol TM 24-L-6 NMW (the condensation product of C$_{12}$–C$_{14}$ primary alcohol with 6 moles ethylene oxide with a narrow molecular weight distribution), both marketed by Union Carbide Corporation; Neodol TM 45-9 (the condensation product of C$_{14}$–C$_{15}$ linear alcohol with 9 moles of ethylene oxide), Neodol TM 23-6.5 (the condensation product of C$_{12}$–C$_{13}$ linear alcohol with 6.5 moles of ethylene oxide), Neodol TM 45-7 (the condensation product of C$_{14}$–C$_{15}$ linear alcohol with 7 moles of ethylene oxide), Neodol TM 45-4 (the condensation product of C$_{14}$–C$_{15}$ linear alcohol with 4 moles of ethylene oxide), marketed by Shell Chemical Company, and Kyro TM EOB (the condensation product of C$_{13}$–C$_{15}$ alcohol with 9 moles ethylene oxide), marketed by The Procter & Gamble Company.

3. The condensation products of ethylene oxide with a hydrophobic base formed by the condensation of propylene oxide with propylene glycol. The hydrophobic portion of these compounds has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic TM surfactants, marketed by Wyandotte Chemical Corporation.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic TM compounds, marketed by Wyandotte Chemical Corporation.

5. Semi-polar nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Preferred semi-polar nonionic detergent surfactants are the amine oxide surfactants having the formula

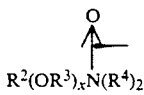

wherein $R^2$ is an alkyl, hydroxyalkyl, or alkyl phenyl group or mixtures thereof containing from about 8 to about 22 carbon atoms; $R^3$ is an alkylene or hydroxyalkylene group containing from about 2 to about 3 carbon atoms or mixtures thereof; x is from 0 to about 3; and each $R^4$ is an alkyl or hydroxyalkyl group containing from about 1 to about 3 carbon atoms or a polyethylene oxide group containing from about 1 to about 3 ethylene oxide groups. The $R^4$ groups can be attached to each other, e.g., through an oxygen or nitrogen atom, to form a ring structure.

Preferred amine oxide surfactants are $C_{10}$–$C_{18}$ alkyl dimethyl amine oxides and $C_8$–$C_{12}$ alkoxy ethyl dihydroxy ethyl amine oxides.

6. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.5 to about 10, preferably from about 1.5 to about 3, most preferably from about 1.6 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6- positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to about 3 hydroxyl groups and/or the polyalkyleneoxide chain can contain up to about 10, preferably less than 5, alkyleneoxide moieties. Suitable alkyl polysaccharides are octyl, nonyl, decyl, undecyl, dodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

The preferred alkylpolyglycosides have the formula

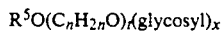

wherein $R^5$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

7. Fatty acid amide surfactants having the formula:

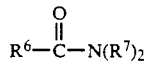

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C_2H_4O)_xH$ where x varies from about 1 to about 3.

Preferred amides are $C_8$–$C_{20}$ ammonia amides, monoethanolamides, diethanolamides, and isopropanolamides.

B. Anionic Detergent Surfactants

Anionic detergent surfactants suitable for use in laundry care compositions containing the product of the present invention are generally disclosed in U.S. Pat. No. 3,929,678, Laughlin et al., issued Dec. 30, 1975, at column 23, line 58 through column 29, line 23 and in U.S. Pat. No. 4,294,710, Hardy et al., issued Oct. 13, 1981, both of which are incorporated herein by reference. Classes of useful anionic surfactants include:

1. Ordinary alkali metal soaps, such as the sodium, potassium, ammonium and alkylolammonium salts of higher fatty acids containing from about 8 to about 24 carbon atoms, preferably from about 10 to about 20 carbon atoms. Preferred alkali metal soaps are sodium laurate, sodium stearate, sodium oleate and potassium palmitate.

2. Water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.)

Examples of this group of anionic surfactants are the sodium and potassium alkylbenzene sulfonates in which the alkyl group contains from about 9 to about 15 carbon atoms, in straight chain or branched chain configuration, e.g., those of the type described in U.S. Pat. No.

2,220,099, Guenther et al., issued Nov. 5, 1940, and U.S. Pat. No. 2,477,383, Lewis, issued Dec. 26, 1946. Especially useful are linear straight chain alkylbenzene sulfonates in which the average number of carbon atoms in the alkyl group is from about 11 to about 13, abbreviated as $C_{11}14\ C_{13}LAS$.

Other anionic surfactants include sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms.

Also included are water-soluble salts of esters of alpha-sulfonated fatty acids containing from about 6 to about 20 carbon atoms in the fatty acid group and from about 1 to about 10 carbon atoms in the ester group; water-soluble salts of 2-acyloxy-alkane-1-sulfonic acids containing from about 2 to about 9 carbon atoms in the acyl group and from about 9 to about 23 carbon atoms in the alkane moiety; alkyl sulfates (AS) containing from about 10 to about 20 carbon atoms in the alkyl group; sulfates such as those of the formula wherein $R^8O(C_2H_4O)_mSO_3M$, wherein $R^8$ is a $C_{10}$-$C_{16}$ alkyl (preferred) or hydroxyalkyl group, m is from about 0.5 to about 4, and M is a compatible cation water-soluble salts of olefin sulfonates containing from about 12 to about 24 carbon atoms; and beta-alkyloxy alkane sulfonates containing from about 1 to about 3 carbon atoms in the alkyl group and from about 8 to about 20 carbon atoms in the alkane moiety. Useful alkylether sulfates are described in detail in U.S. Pat. No. 4,807,219, to Hughes, issued Mar. 26, 1985, which is incorporated herein by reference. The above surfactant preferably represent from about 8% to about 18%, by weight (on an acid basis) of the composition, more preferably from about 9% to about 14%.

Preferred alkylethoxylated sulfate surfactants of the above formula are those wherein the $R^8$ substituent is a $C_{12}$-$C_{15}$ alkyl group and m is from about 1.5 to about 3. Examples of such materials are $C_{12}$-$C_{15}$ alkyl polyethoxylate (2.25) sulfate ($C_{12-15}E_{2.25}S$); $C_{14-15}E_{2.25}S$; $C_{12-13}E_{1.5}S$: $C_{14-15}E_3S$; and mixtures thereof.

Particularly preferred surfactants for use in liquid detergent composition are linear $C_{11}$ to $C_{13}$ alkyl benzene sulfonates, alkyl sulfates, and alkylethoxylated sulfates (anionic) and $C_{12}$ to $C_{13}$ alkyl polyethoxylated alcohols (nonionic) and mixtures thereof. Liquid detergent compositions which contain alkyl and/or alkylethoxylated sulfates as detergent surfactants preferably comprise no more than about 5% of such detergent surfactants, and the anionic compound of the ion-pair complex is most preferably a $C_1$-$C_3$ LAS or benzene sulfonate. Particularly preferred surfactants for use in granular detergents are the linear $C_{11}$-$C_{13}$ alkyl benzene sulfonates and the $C_8$-$C_{18}$ alkyl sulfates and mixtures thereof. Most preferred are mixtures of these two anionic surfactants in a weight ratio of linear alkyl benzene sulfonate to alkyl sulfate is from about 0.5:1 to about 3:1 and more preferably from about 0.5:1 to about 2:1.

3. Anionic phosphate surfactants.
4. N-alkyl substituted succinamates.

C. Ampholytic Surfactants

Ampholytic surfactants can be broadly described as aliphatic derivatives of secondary or tertiary amines, or aliphatic derivatives of heterocyclic secondary and tertiary amines in which the aliphatic radical can be straight or branched chain and wherein one of the aliphatic substituents contains from about 8 to about 18 carbon atoms and at least one of the aliphatic substituents contains an anionic water-solubilizing group, e.g., carboxy, sulfonate, sulfate. See U.S. Pat. No. 3,929,678, Laughlin et al., issued Dec. 30, 1975, column 19, line 38 through column 22, line 48, incorporated herein by reference, for examples of ampholytic surfactants useful herein.

D. Zwitterionic Surfactants

Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678, Laughlin et al., issued Dec. 30, 1975, column 19, line 38 through column 22, line 48, incorporated herein by reference, for examples of zwitterionic surfactants useful herein.

E. Cationic Surfactants

Cationic surfactants are also useful in laundry care compositions containing the product of the process of the present invention. Cationic surfactants comprise a wide variety of compounds characterized by one or more organic hydrophobic groups in the cation and generally by a quaternary nitrogen associated with an acid radical. Pentavalent nitrogen ring compounds are also considered quaternary nitrogen compounds. Suitable anions are halides, methyl sulfate and hydroxide. Tertiary amines can have characteristics similar to cationic surfactants at washing solutions pH values less than about 8.5.

Suitable cationic surfactants include the quaternary ammonium surfactants having the formula:

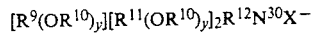

$$[R^9(OR^{10})_y][R^{11}(OR^{10})_y]_2R^{12}N^{30}X^-$$

wherein is an alkyl or alkyl benzyl group having from about 8 to about 18 carbon atoms in the alkyl chain; each $R^{10}$ is in. dependently selected from the group consisting of $-CH_2CH_2-$, $-CH_2CH(CH_3)-$, $-CH_2CH(CH_2OH)-$, and $-CH_2CH_2CH_2-$; each $R^{11}$ is independently selected from the group consisting of $C_1$-$C_4$ alkyl, $C_1$-$C_4$ hydroxyalkyl, benzyl, ring structures formed by joining the two $R^{11}$ groups, $-CH_2$-$CHOHCHOHCOR^{13}CHOHCH_2OH$ wherein $R^{13}$ is any hexose or hexose polymer having a molecular weight less than about 1000, and hydrogen when y is not 0; $R^{12}$ is the same as $R^{11}$ or is an alkyl chain wherein the total number of carbon atoms of $R^9$ plus $R^{12}$ is not more than about 18; each y is from 0 to about 10 and the sum of the y values is from 0 to about 15; and X is any compatible anion.

Preferred examples of the above compounds are the alkyl quaternary ammonium surfactants, especially the mono-long chain alkyl surfactants described in the above formula when $R^{12}$ is selected from the same groups as $R^{11}$. The most preferred quaternary ammonium surfactants are the chloride, bromide and methylsulfate $C_8$-$C_{16}$ alkyl trimethylammonium salts, $C_8$-$C_{16}$ alkyl di(hydroxyethyl)methylammonium salts, the $C_8$-$C_{16}$ alkyl hydroxyethyldimethylammonium salts, and $C_8$-$C_{16}$ alkyloxypropyltrimethylammonium salts. Of the above, decyl trimethylammonium methylsulfate, lauryl trimethylammonium chloride, myristyl trimethylammonium bromide and coconut trimethylammonium chloride and methylsulfate are particularly preferred.

A more complete disclosure of these and other cationic surfactants useful herein can be found in U.S. Pat. No. 4,228,044, Cambre, issued Oct. 14, 1980, incorporated herein by reference.

Detergent Builders

Laundry care compositions containing the product of the process of the present invention can also contain inorganic and/or organic detergent builders to assist in mineral hardness control. These builders comprise from 0% to about 80% by weight of the compositions. Liquid formulations preferably comprise from about 5% to about 50%, more preferably about 5% to about 30%, by weight of detergent builder. Granular formulations preferably comprise from about 10% to about 80%, more preferably from about 24% to about 80% by weight of the detergent builder.

Useful water-soluble organic builders for granular and liquid compositions include the various alkali metal, ammonium and substituted ammonium polyacetates, carboxylates, polycarboxylates and polyhydroxysulfonates. Examples of polyacetate and polycarboxylate builders are the sodium, potassium, lithium, ammonium and substituted ammonium salts of ethylenediamine tetraacetic acid, nitrilotriacetic acid, oxydisuccinic acid, mellitic acid, benzene polycarboxylic acids, and citrate. The citrate (preferably in the form of an alkali metal or alkanolammonium salt) is generally added to the composition as citric acid, but can be added in the form of a fully neutralized salt.

Highly preferred polycarboxylate builders are disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Other builders include the carboxylated carbohydrates disclosed in U.S. Pat. No. 3,723,322, Diehl, issued Mar. 28, 1973, incorporated herein by reference.

A class of useful phosphorus-free detergent builder materials have been found to be ether polycarboxylates. A number of ether polycarboxylates have been disclosed for use as detergent builders. Examples of useful ether polycarboxylates include oxydisuccinate, as disclosed in Berg, U.S. Pat. No. 3,128,287, issued Apr. 7, 1964, and Lamberti et al, U.S. Pat. No. 3,635,830, issued Jan. 18, 1972, both of which are incorporated herein by reference.

A specific type of ether polycarboxylates useful as builders in the present invention are those having the general formula:

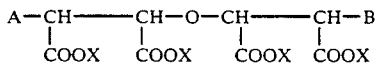

wherein A is H or OH; B is H or

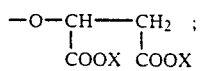

and X is H or a salt-forming cation. For example, if in the above general formula A and B are both H, then the compound is oxydisuccinic acid and its water-soluble salts. If A is OH and B is H, then the compound is tartrate monosuccinic acid (TM S) and its water-soluble salts. If A is H and B is

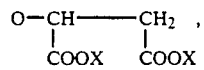

then the compound is tartrate disuccinic acid (TDS) and its water-soluble salts. Mixtures of these builders are especially preferred for use herein. Particularly preferred are mixtures of TM S and TDS in a weight ratio of TM S to TDS of from about 97:3 to about 20:80. These builders are disclosed in U.S. Pat. No. 4,663,071, issued to Bush et al., on May 5, 1987.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

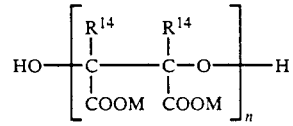

wherein M is hydrogen or a cation wherein the resultant salt is water-soluble, preferably an alkali metal, ammonium or substituted ammonium cation, n is from about 2 to about 15 (preferably n is from about 2 to about 10, more preferably n averages from about 2 to about 4) and each $R^{14}$ is the same or different and selected from hydrogen, $C_{1-4}$ alkyl or $C_{1-4}$ substituted alkyl (preferably $R^{14}$ is hydrogen). Also suitable in such laundry care compositions are the 3,3-dicarboxy-4-oxa-],6 hexanedioates and the related compounds disclosed in U.S. Pat. No. 4,566,984, Bush, issued Jan. 28, 1986, incorporated herein by reference. Other useful builders include the $C_5$–$C_{20}$ alkyl succinic acids and salts thereof. A particularly preferred compound of this type is dodecenylsuccinic acid.

Useful builders also include sodium and potassium carboxymethyloxymalonate, carboxymethyloxysuccinate, cis-cyclohexanehexacarboxylate, cis-cyclopentanetetracarboxylate phloroglucinol trisulfonate, water-soluble polyacrylates (having molecular weights of from about 2,000 to about 200,000, for example), and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal boxylate ester is then attached to chemically stable end groups to stabilize the polyacetal carboxylate against rapid depolymerization in alkaline solution, converted to the corresponding salt, and added to a surfactant.

Especially useful builders include alkyl succinates of the general formula $R^{15}$–CH(COOH)CH$_2$(COOH) i.e., derivatives of succinic acid, wherein $R^{15}$ is hydrocarbon, e.g., $C_{10}$-$C_{20}$ alkyl or alkenyl, preferably $C_{12}$-$C_{16}$ or wherein $R^{15}$ may be substituted with hydroxyl, sulfo, sulfoxy or sulfone substituents, all as described in the above-mentioned patents.

The succinate builders are preferably used in the form of their water-soluble salts, including the sodium, potassium, ammonium and alkanolammonium salts.

Specific examples of succinate builders include: lauryl succinate, myristyl succinate, palmityl succinate, 2-dodecenyl succinate (preferred), 2-pentadecenyl succinate, and the like.

Other useful detergency builders include the $C_{10}$-$C_{18}$ alkyl monocarboxylic (fatty) acids and salts thereof. These fatty acids can be derived from animal and vegetable fats and oils, such as tallow, coconut oil and palm oil. Suitable saturated fatty acids can also be synthetically prepared (e.g., via the oxidation of petroleum or by hydrogenation of carbon monoxide via the Fisher-Tropsch process). Particularly preferred $C_{10}$-$C_{18}$ alkyl monocarboxylic acids are saturated coconut fatty acids, palm kernel fatty acids, and mixtures thereof.

Chelating Agents

The detergent compositions herein may also optionally contain one or more iron and manganese chelating agents. Such chelating agents can be selected from the group consisting of amino carboxylates, amino phosphonates, polyfunctionally—substituted aromatic chelating agents and mixtures thereof, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents in compositions of the invention have one or more, preferably at least two, units of the substructure

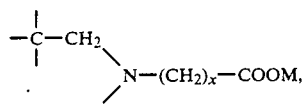

wherein M is hydrogen, alkali metal, ammonium or substituted ammonium (e.g. ethanolamine) and x is from 1 to about 3, preferably 1. Preferably, these amino carboxylates do not contain alkyl or alkenyl groups with more than about 6 carbon atoms. Operable amine carboxylates include ethylenediaminetetraacetates, N-hydroxyethylethylenediaminetriacetates, nitrilotriacetates, ethylenediamine tetraproprionates, triethylenetetraaminehexaacetates, diethylenetriaminepentaacetates, and ethanoldiglycines, alkali metal, ammonium, and substituted ammonium salts thereof and mixtures thereof.

Amino phosphonates are also suitable for use as chelating agents in the compositions of the invention when at least low levels of total phosphorus are permitted in detergent compositions. Compounds with one or more, preferably at least two, units of the substructure

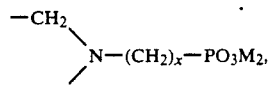

wherein M is hydrogen, alkali metal, ammonium or substituted ammonium and x is from 1 to about 3, preferably 1, are useful and include ethylenediaminetetrakis (methylenephosphonates), nitrilotris (methylenephosphonates) and diethylenetriaminepentakis (methylenephosphonates). Preferably, these amino phosphonates do not contain alkyl or alkenyl groups with more than about 6 carbon atoms. Alkylene groups can be shared by substructures.

Polyfunctionally—substituted aromatic chelating agents are also useful in the compositions herein. These materials comprise compounds having the general formula

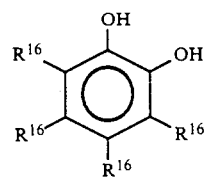

wherein at least one $R_{16}$ is —$SO_3H$ or —COOH or soluble salts thereof and mixtures thereof. U.S. Pat. No. 3,812,044, issued May 21, 1974, to Connor et al., incorporated herein by reference, discloses polyfunctionally—substituted aromatic chelating and sequestering agents. Preferred compounds of this type in acid form are dihydroxydisulfobenzenes and 1,2-dihydroxy-3,5-disulfobenzene or other disulfonated catechols in particular. Alkaline detergent compositions can contain these materials in the form of alkali metal, ammonium or substituted ammonium (e.g. mono- or tri-ethanolamine) salts.

If utilized, these chelating agents will generally comprise from about 0.1% to about 10% by weight of the detergent compositions herein. More preferably chelating agents will comprise from about 0.1% to about 3.0% by weight of such compositions.

Soil Release Agent

Polymeric soil release agents useful in the present invention include cellulosic derivatives such as hydroxyether cellulosic polymers, copolymeric blocks of ethylene terephthalate and polyethylene oxide or polypropylene oxide terephthalate, and cationic guar gums, and the like.

The cellulosic derivatives that are functional as soil release agents are commercially available and include hydroxyethers of cellulose such as Methocel ® (Dow) and cationic cellulose ether derivatives such as Polymer JR-124 ®, JR-400 ®, and JR-30M ® (Union Carbide). See also U.S. Pat. No. 3,928,213 to Temple et al., issued Dec. 23, 1975, which is incorporated by reference.

Other effective soil release agents are cationic guar gums such as Jaguar Plau ® (Stein Hall) and Gendrive 458 ® (General Mills).

Preferred cellulosic soil release agents for use herein are selected from the group consisting of methyl cellulose; hydroxypropyl methylcellulose; hydroxybutyl methylcellulose; or a mixture thereof, said cellulosic polymer having a viscosity in aqueous solution at 20° C. of 15 to 75,000 centipoise.

A more preferred soil release agent is a copolymer having random blocks of ethylene terephthalate and polyethylene oxide (PEO) terephthalate. More specifically, these polymers are comprised of repeating units of ethylene terephthalate and PEO terephthalate in a mole ratio of ethylene terephthalate units to PEO terephthalate units of from about 25:75 to about 35:65, said PEO terephthalate units containing polyethylene oxide having molecular weights of from about 300 to about 2000. The molecular weight of this polymeric soil release agent is in the range of from about 25,000 to about 55,000. See U.S. Pat. No. 3,959,230 to Hays, issued May 25, 1976, which is incorporated by reference. See also U.S. Pat. No. 3,893,929 to Basadur issued July 8, 1975 (incorporated by reference) which discloses similar copolymers. Surprisingly, it has been found that these polymeric soil release agents balance the distribution of the fabric care agent of the present invention against a broad range of synthetic fabrics such as polyesters, nylons, poly cottons and acrylics. This more uniform distribution of the fabric care agent can result in improved fabric care qualities.

Another preferred polymeric soil release agent is a crystallizable polyester with repeat units of ethylene terephthalate units containing 10–15% by weight of ethylene terephthalate units together with 90–80% by weight of polyoxyethylene terephthalate units, derived from a polyoxyethylene glycol of average molecular weight 300–5,000, and the mole ratio of ethylene terephthalate units to polyoxyethylene terephthalate units in the crystallizable polymeric compound is between 2:1 and 6:1. Examples of this polymer include the commercially available material Zelco ® 5126 (from Dupont) and Milease ® T (from ICI).

The foregoing polymers and methods of their preparation are more fully described in European Pat. No. Application 185,417, Gosselink, published June 25, 1986, which is incorporated herein by reference.

If utilized, these soil release agents will generally comprise from about 0.01% to about 5.0% by weight of the detergent compositions herein, more preferably soil release agents will comprise from about 0.2% to about 3.0% by weight of such compositions.

Enzymes

Enzymes are a preferred optional ingredient and are incorporated in an amount of from about 0.025% to about 2%, preferably from about 0.05% to about 1.5% of the total composition. Preferred proteolytic enzymes should provide a proteolytic activity of at least about 5 Anson units (about 1,000,000 Delft units) per liter, preferably from about 15 to about 70 Anson units per liter, most preferably from about 20 to about 40 Anson units per liter. A proteolytic activity of from about 0.01 to about 0.05 Anson units per gram of product is desirable. Other enzymes, including amylolytic enzymes, are also desirably included in the present compositions.

Suitable proteolytic enzymes include the many species known to be adapted for use in detergent compositions. Commercial enzyme preparations such as Savinase ™ and Alcalase ™ sold by Novo Industries and Maxatase ™ sold by Gist-Brocades, Delft, The Netherlands, are suitable. Other preferred enzyme compositions include those commercially available under the tradenames SP-72 (Esperase ™) manufactured and sold by Novo Industries, A/S, Copenhagen, Denmark and AZ-Protease ™ manufactured and sold by Gist-Brocades, Delft, The Netherlands.

Suitable amylases include Rapidase ™ sold by Gist-Brocades and Termamyl ™ sold by Novo Industries.

A more complete disclosure of suitable enzymes can be found in U.S. Pat. No. No. 4,101,457, Place et al., issued July 18, 1978, and in U.S. Pat. No. 4,507,219, Hughes, issued Mar. 26, 1985, both incorporated herein by reference.

Other Optional Detergent Ingredients

Other optional ingredients which can be included in detergent compositions of the present invention, in their conventional art-established levels for use (generally from 0 to about 20%), include solvents, hydrotropes, solubilizing agents, suds suppressors, processing aids, soil-suspending agents, corrosion inhibitors, dyes, fillers, optical brighteners, germicides, pH-adjusting agents (monoethanolamine, sodium carbonate, sodium hydroxide, etc.), enzyme-stabilizing agents, bleaches, bleach activators, clay fabric softeners, perfumes, and the like.

Product Formulations

1. Liquid Compositions

Liquid detergent compositions containing the product of the process of the present invention can contain water and other solvents. Small quantities of low molecular weight primary or secondary alcohols, exemplified by methanol, ethanol, propanol, and isopropanol, are suitable solvents. Liquid compositions may comprise the product of the process of the present invention as the only fabric care agent, or this agent may be combined with other fabric care agents. The active components of the liquid composition may primarily be fabric conditioning agents, may include detergent ingredients such as those disclosed herein, and may include other cleaning, conditioning, or other ingredients not specifically listed herein.

With liquid detergent compositions it is preferred to include monohydric alcohols for solubilizing the surfactant, but polyols containing from about 2 to about 6 carbon atoms and from about 2 to about 6 hydroxyl groups can be used and can provide improved enzyme stability (if enzymes are included in the composition). Examples of polyols include propylene glycol, ethylene glycol, glycerine and 1,2-propanediol. Propylene glycol is a particularly preferred alcohol.

Other optional components of these liquid conditioning compositions of this type are conventional in nature, and generally comprise from about 0.1% to about 20% by weight of the composition. Such optional components for fabric conditioners include, but are not limited to, colorants, perfumes, bacterial inhibitors, optical brighteners, opacifiers, viscosity modifiers, fabric absorbency boosters, emulsifiers, stabilizers, shrinkage controllers, spotting agents, germicides, fungicides, anti-corrosion agents and the like.

The ratios of water and other solvents in the compositions will be determined in part by the resulting state of the fabric care agent. At ambient temperatures, the fabric care agent must be substantially insoluble in the product, and within the particle size specifications heretofore discussed. This will place restrictions upon the selection of solvents and solvent levels in the compositions.

The liquid fabric conditioning compositions of the present invention can be prepared by conventional methods.

2. Granular Compositions

Granular detergent compositions may comprise the product of the process of the present invention as the only fabric conditioning agent, or this agent may be combined with other fabric conditioning agents. The active components of the granular composition may primarily be fabric conditioning agents, may include detergent ingredients such as those disclosed herein, and may include cleaning, conditioning, or other ingredients not specifically listed herein.

Granular detergent compositions embodying the present invention can be formed by conventional techniques, i.e., by slurrying the individual components (with the exception of the ion-pair complex) in water and then atomizing and spray-drying the resultant mixture, or by pan or drum agglomeration of the ingredients.

In a laundry method aspect of the invention, typical laundry wash water solutions comprise from about 0.1% to about 2% by weight of the detergent compositions of the invention. Fabrics to be laundered are agitated in these solutions to effect cleaning, stain removal, and fabric care benefits.

The conditioning agents of the invention are particularly suitable for laundry use, but are also suitable as a hair conditioning component in shampoos and hair conditioning compositions.

The foregoing description fully describes the nature of the present invention. The following examples are presented for the purpose of illustrating the invention. The scope of the invention is to be determined by the claims, which follow the examples.

All parts, percentages and ratios herein are by weight unless otherwise specified.

EXAMPLE I

An unsaturated fatty sulfate compound is prepared as follows: 2.67 g of oleyl alcohol is combined with 10.0 ml of diethyl ether, with agitation, to form an initial solution. 1.78 g of the compound $CH_3OCH_2CH_2OSO_3Na$ is added to this solution, with agitation, to form a heterogeneous reaction mixture. This heterogeneous reaction mixture is stirred vigorously with a mechanical stirrer while adding 0.05 g of sulfuric acid to form a final reaction mixture. The final reaction mixture is stirred at ambient temperature for 18 hours. The final reaction product will comprise starting material, the compound $CH_3(CH_2)_7CH=CH(CH_2)_8OSO_3Na$ and the alcohol $CH_3OCH_2CH_2OH$.

EXAMPLE II

An unsaturated fatty sulfate compound is prepared as follows: 2.39 g of cis-11-hexadecen-1-ol is combined with 10.0 ml of dioxane, with agitation, to form an initial solution. 3.54 g of the compound $CH_3(OCH_2CH_2)_5OSO_3Na$ is added to this solution, with agitation, to form a heterogeneous reaction mixture. This heterogeneous reaction mixture is stirred vigorously with a mechanical stirrer while adding 0.5 g of Amberlyst® 15 ionic-exchange resin (available from the Aldrich Chemical Company, Inc., Milwaukee, Wisconsin) to form a final reaction mixture. The final reaction mixture is stirred at ambient temperature for 18 hours. The final reaction product will comprise starting material, the compound $CH_3(CH_2)_3CH=CH(CH_2)_{10}OSO_3Na$ and the alcohol $CH_3(OCH_2CH_2)_5OH$.

EXAMPLE III

An unsaturated fatty sulfate compound is prepared as follows: 2.95 g of 3,7,11,15-tetramethyl-2-hexadecen-1-ol is combined with 10.0 ml of methylene chloride, with agitation, to form an initial solution. 4.80 g of the compound $CH_3(CH_2)_9(OCH_2CH_2)_5OSO_3Na$ is added to this solution, with agitation, to form a heterogeneous reaction mixture. This heterogeneous reaction mixture is stirred vigorously with a mechanical stirrer while adding 0.09 g of toluene sulfonic acid to form a final reaction mixture. The final reaction mixture is stirred at ambient temperature for 18 hours. The final reaction product will comprise starting material, the compound $CH_3[CH(CH_3)(CH_2)_3]_3C(CH_3)=CHCH_2OSO_3Na$ and the alcohol $CH_3(CH_2)_9(OCH_2CH_2)_5OH$.

EXAMPLE IV

An unsaturated fatty sulfate compound is prepared as follows: 2.11 g of cis-7-tetradecen-1-ol is combined with 10.0 ml of hexane, with agitation, to form an initial solution. 3.36 g of the compound $CH_3(CH_2)_5(OCH_2CH_2)_3OSO_3Na$ is added to this solution, with agitation, to form a heterogeneous reaction mixture. This heterogeneous reaction mixture is stirred vigorously with a mechanical stirrer while adding 0.12 g of camphorsulfonic acid to form a final reaction mixture. The final reaction mixture is stirred at ambient temperature for 18 hours. The final reaction product will comprise starting material, the compound $CH_3(CH_2)_5CH=CH(CH_2)_6OSO_3Na$ and the alcohol $CH_3(CH_2)_5(OCH_2CH_2)_3OH$.

EXAMPLE V

An unsaturated fatty sulfate compound is prepared as follows: 2.67 g of oleyl alcohol is combined with of 1.78 g of the compound $CH_3OCH_2CH_2OSO_3Na$, with agitation, to form a heterogeneous reaction mixture. This heterogeneous reaction mixture is stirred vigorously with a mechanical stirrer while adding 0.05 g of sulfuric acid to form a final reaction mixture. The final reaction mixture is stirred at ambient temperature for 18 hours. The final reaction product will comprise starting material, the compound $CH_3(CH_2)_7CH=CH(CH_2)_8OSO_3Na$ and the alcohol $CH_3OCH_2CH_2OH$.

EXAMPLE VI

An unsaturated fatty sulfate compound is prepared as follows: 2.39 g of cis-11-hexadecen-1-ol is combined with 3.54 g of the compound $CH_3(OCH_2CH_2)_5OSO_3Na$, with agitation, to form a heterogeneous reaction mixture. This heterogeneous reaction mixture is stirred vigorously with a mechanical stirrer at a temperature of 27° C. while adding 0.5 g of Amberlyst® 15 ionic-exchange resin (available from the Aldrich Chemical Company, Inc., Milwaukee, Wis.) to form a final reaction mixture. The final reaction mixture is stirred at a temperature of 27° C. for 18 hours. The final reaction product will comprise starting material, the compound $CH_3(CH_2)_3CH=CH(CH_2)_{10}OSO_3Na$ and the alcohol $CH_3(OCH_2CH_2)_5OH$.

EXAMPLE VII

An unsaturated fatty sulfate compound is prepared as follows: 2.95 g of 3,7,11,15-tetramethyl-2-hexadecen-1- ol is combined with 4.80 g of the compound $CH_3(CH_2)_9(OCH_2CH_2)_5OSO_3Na$, with agitation, to form a heterogeneous reaction mixture. This heterogeneous reaction mixture is stirred vigorously with a mechanical stirrer while adding 0.09 g of toluene sulfonic acid to form a final reaction mixture. The final reaction mixture is stirred at ambient temperature for 18 hours. The final reaction product will comprise starting material, the compound $CH_3[CH(CH_3)(CH_2)_3]_3C(CH_3)=CHCH_2OSO_3Na$ and the alcohol $CH_3(CH_2)_9(OCH_2CH_2)_5OH$.

EXAMPLE VIII

An unsaturated fatty sulfate compound is prepared as follows: 2.11 g of cis-7-tetradecen-1-ol is combined with 3.36 g of the compound $CH_3(CH_2)_5(OCH_2CH_2)_3OSO_3Na$, with agitation, to form a heterogeneous reaction mixture. This heterogeneous reaction mixture is stirred vigorously with a mechanical stirrer at a temperature of 27° C. while adding 0.12 g of camphorsulfonic acid to form a final reaction mixture. The final reaction mixture is stirred at a temperature of 27° C for 18 hours. The final reaction product will comprise starting material, the compound $CH_3(CH_2)_5CH=CH(CH_2)_6OSO_3Na$ and the alcohol $CH_3(CH_2)_5(OCH_2CH_2)_3OH$.

What is claimed is:

1. A process for sulfating unsaturated alcohols comprising reacting an unsaturated alcohol of the formula R—OH, wherein R is a $C_8$-$C_{22}$ alkenyl group, with an ether sulfate of the formula $R^1(OCH_2CH_2)_nOSO_3M$, wherein $R^1$ is a $C_1$-$C_{18}$ hydrocarbyl group, n is an integer ranging from 1 to 10, and M is an alkali metal, and wherein the mole ratio of unsaturated alcohol reactant to ether sulfate reactant ranges from about 0.5:1 to about 2:1, to form an unsaturated sulfate compound of the formula R—$OSO_3M$; said reaction being carried out in the presence of a catalytically effective amount of an acid catalyst.

2. A process according to claim 1 wherein R is a $C_{15}$-$C_{21}$ alkenyl group.

3. A process according to claim 2 wherein R is a $C_{18}$ alkenyl group.

4. A process according to claim 2 wherein $R^1$ is a $C_1$-$C_6$ alkyl group.

5. A process according to claim 4 wherein $R^1$ is a methyl group.

6. A process according to claim 4 wherein n ranges from 1 to 4.

7. A process according to claim 6 wherein n is 1.

8. A process according to claim 6 wherein M is sodium.

9. A process according to claim 6 wherein the acid catalyst is selected from the group consisting of sulfuric acid, toluene sulfonic acid and methane sulfonic acid, and the mole ratio of acid catalyst to unsaturated alcohol reactant ranges from about 1:100 to about 1:5.

10. A process according to claim 9 wherein the acid catalyst is sulfuric acid and the mole ratio of acid catalyst to unsaturated alcohol reactant is about 1:20.

11. A process according to claim 4 wherein the mole ratio of unsaturated alcohol reactant to ether sulfate reactant ranges from about 0.66:1 to about 1.5:1.

12. A process according to claim 10 wherein the mole ratio of unsaturated alcohol reactant to ether sulfate reactant is about 1:1.

13. A process according to claim 12 wherein R is a $C_{18}$ alkenyl group, $R^1$ is a methyl group, n is 1 and M is sodium.

14. A process according to claim 6 wherein the reaction between the unsaturated alcohol and the ether sulfate is carried out for a period of time ranging from about 12 hours to about 36 hours.

15. A process according to claim 14 wherein the reaction between the unsaturated alcohol and the ether sulfate is carried out for a period of about 18 hours.

16. A process according to claim 6 wherein the final reaction product comprises from about 8% to about 12% by weight of the unsaturated sulfate compound of the formula R—$OSO_3M$; from about 5% to about 15% by weight of the ethoxylated alcohol compound of the formula $R^1(OCH_2CH_2)_nOH$; from about 0.2% to about 2% by weight of the acid catalyst; and from about 30% to about 65% by weight of solvent.

17. A process according to claim 16 wherein the solvent contained in the final reaction product is diethyl ether.

18. A process according to claim 17 wherein the final reaction product comprises about 10% by weight of the unsaturated sulfate compound; about 8% by weight of the ethoxylated alcohol compound; about 0.4% by weight of the acid catalyst; and about 60% by weight of solvent.

* * * * *